US010543334B2

(12) United States Patent
Biba

(10) Patent No.: US 10,543,334 B2
(45) Date of Patent: Jan. 28, 2020

(54) APPARATUS AND METHOD FOR DETECTING LIQUID LEVEL IN A CLEAR OR PARTIALLY CLEAR CONTAINER

(71) Applicant: Mallinckrodt Hospital Products IP Limited, Dublin (IE)

(72) Inventor: Scott I. Biba, Waunakee, WI (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 321 days.

(21) Appl. No.: 15/460,334

(22) Filed: Mar. 16, 2017

(65) Prior Publication Data

US 2017/0319809 A1    Nov. 9, 2017

Related U.S. Application Data

(60) Provisional application No. 62/331,117, filed on May 3, 2016.

(51) Int. Cl.
*A61M 16/08* (2006.01)
*A61M 16/10* (2006.01)
(Continued)

(52) U.S. Cl.
CPC .... *A61M 16/0808* (2013.01); *A61M 16/1005* (2014.02); *A61M 16/107* (2014.02);
(Continued)

(58) Field of Classification Search
CPC .......... A61M 16/0808; A61M 16/1005; A61M 16/107; A61M 2016/102; A61M 2205/14; A61M 2205/3306; A61M 2205/3379; A61M 2205/3382; A61M 2205/3386; A61M 2205/6063
See application file for complete search history.

(56) References Cited

U.S. PATENT DOCUMENTS 4,028,444 A    6/1977  Brown et al.
5,826,575 A *  10/1998 Lall .......................... A61B 5/097
                                                    128/205.12
(Continued)

FOREIGN PATENT DOCUMENTS

EP    1873501    1/2008

OTHER PUBLICATIONS

Definition of Circumferential (Dictionary.com Mar. 29, 2019) (Year: 2019).*
(Continued)

*Primary Examiner* — Nathan R Price
*Assistant Examiner* — Dung T Ulsh

(57) ABSTRACT

A trap bowl is provided to accumulate liquid droplets from a filter, as a liquid content. The trap bowl includes a transparent vertical prism. The transparent vertical prism includes a face that forms a vertical transparent surface facing against a content of the section. The face can provide a first angle of total reflection when content of the section is a type of gas, and a second angle of total reflection when the content of the section is the liquid content. A light source may emit a light beam incident on the face at an angle of incidence. The angle of incidence results in reflection of the light beam, striking the light receiver, when the face has the first angle of total reflection, and results in refraction of the light beam, missing the light receiver, when the face has the second angle of total reflection.

8 Claims, 13 Drawing Sheets

(51) Int. Cl.
  *B01D 46/00*   (2006.01)
  *G01F 23/292*   (2006.01)
(52) U.S. Cl.
  CPC ..... *B01D 46/0002* (2013.01); *B01D 46/0023* (2013.01); *B01D 46/0086* (2013.01); *G01F 23/2921* (2013.01); *A61M 2016/102* (2013.01); *A61M 2205/14* (2013.01); *A61M 2205/3306* (2013.01); *A61M 2205/3379* (2013.01)

(56) References Cited

U.S. PATENT DOCUMENTS

| | | | | |
|---|---|---|---|---|
| 2003/0167927 | A1* | 9/2003 | Ostberg | A61M 16/0808 |
| | | | | 96/414 |
| 2006/0139384 | A1* | 6/2006 | Kitabatake | B41J 2/17553 |
| | | | | 347/7 |
| 2008/0066542 | A1* | 3/2008 | Gao | G01F 23/292 |
| | | | | 73/290 R |
| 2008/0114301 | A1 | 5/2008 | Bandhauer et al. | |
| 2010/0134303 | A1* | 6/2010 | Perkins | A61M 5/14 |
| | | | | 340/619 |
| 2013/0345573 | A1* | 12/2013 | Kargar | A61B 5/021 |
| | | | | 600/485 |
| 2016/0015885 | A1* | 1/2016 | Pananen | A61M 5/142 |
| | | | | 604/111 |

OTHER PUBLICATIONS

International Search Report and Written Opinion of the International Searching Authority, dated May 29, 2017.

* cited by examiner

Top view of water trap bowl

APPARATUS AND METHOD FOR DETECTING LIQUID LEVEL IN A CLEAR OR PARTIALLY CLEAR CONTAINER

CROSS-REFERENCE TO RELATED APPLICATION

This application claims priority to U.S. Patent Application No. 62/331,117, filed on May 3, 2016, and entitled "APPARATUS AND METHOD FOR DETECTING LIQUID LEVEL IN A CLEAR OR PARTIALLY CLEAR CONTAINER," the contents of which are incorporated herein by reference in their entirety.

FIELD

The present disclosure generally relates to the removal (e.g., filtering) and collection in a container or trap of liquid particles from sampled inspiratory gas flow of a patient breathing circuit affiliated with a ventilator and/or therapeutic gas delivery system (e.g., inhaled nitric oxide gas delivery system).

BACKGROUND

An array of patients can benefit from receiving therapeutic gas (e.g., nitric oxide gas) in inspiratory breathing gas flow. The therapeutic gas can be delivered, for example, from a breathing circuit affiliated with a ventilator (e.g., constant flow ventilator, variable flow ventilator, high frequency ventilator, bi-level positive airway pressure ventilator or BiPAP ventilator, etc.). In operation, therapeutic gas may be injected into the inspiratory breathing gas flowing in the breathing circuit of the ventilator device. This inhaled therapeutic gas is often provided via a therapeutic gas delivery system at a constant concentration, which is provided based on proportional delivery of the therapeutic gas to the breathing gas. Further, a sampling system (e.g., affiliated the therapeutic gas delivery system) may continuously draw in the inspiratory breathing gas flow to at least confirm that the desired dose of the therapeutic gas in the inspiratory breathing gas flow is being delivered to the patient. Example operation can include a sample pump pulling in inspiratory flow (e.g., in the near vicinity of the patient) to confirm that the desired therapeutic gas concentration is in fact being delivered to the patient.

One such therapeutic gas is inhaled nitric oxide (iNO), which can be used as a therapeutic gas to produce vasodilatory effect on patients. When inhaled, iNO acts to dilate blood vessels in the lungs, improving oxygenation of the blood and, for example, reducing pulmonary hypertension. Accordingly, nitric oxide is provided in inspiratory breathing gases for patients with various pulmonary pathologies including, but not limited to, hypoxic respiratory failure (HRF) and persistent pulmonary hypertension (PPH). The actual administration of iNO is generally carried out by introduction into the patient as a gas along with other normal inhalation gases. For example, iNO can be introduced, from an iNO delivery system, into the inspiratory flow of a patient breathing circuit affiliated with a ventilator.

Separately and/or in conjunction with iNO, patients may receive inspiratory breathing gas flow containing liquid particles (e.g., nebulized medical solutions and suspensions, moisture from humidified air, etc.) and/or other particles. However, as described above, iNO delivery systems may include a sampling system to confirm dosing of iNO being delivered to the patient. Liquid particles in the inspiratory breathing flow, even though they may provide additional benefit to the patient, may contaminate the sampling system (e.g., gas analyzers). Accordingly, at times, there is a need to filter the sampled inspiratory breathing gas flow of liquid particles and/or other particles, for purposes such as mitigating contamination of the gas sampling system.

Associated with filtering liquid particles from the inspiratory breathing flow, there is a need to trap the liquid particles that are removed. Various configurations of such traps, and various techniques directed to detecting the fluid level in the traps, are known. Additional desired features of the level detection may include tolerance for various orientations of the trap, ability to detect proper installation of the trap, simplicity, and ready adaptability to different capacities of traps. Accordingly, there is a need for an improved apparatus and method to trap, and detect accumulated levels of liquid particles filtered from inspiratory breathing gas flow being provided to a patient in need thereof.

SUMMARY

Generally speaking, aspects of the present disclosure relate to filtration apparatuses and methods to remove liquid particles from a gas stream containing humidity, water vapor, nebulized liquid or other liquid components. Particulates may also be removed. More specifically, aspects of the present disclosure relate to filtration devices and methods to remove liquid particles and/or particles from sampled inspiratory gas flow of a patient breathing circuit affiliated with a ventilator and/or therapeutic gas delivery system (e.g., inhaled nitric oxide gas delivery system).

One or more disclosed embodiments pertain to a filter trap apparatus that, in aspect, can include a trap bowl configured to accumulate liquid droplets from a filter, as a liquid content, and that can have or provide an associated transparent circumferential prism. The face, in an aspect, can form a circumferential interior surface of the trap bowl. The face, according to one or more implementations, can provide a first angle of total reflection when the gas is against the circumferential interior surface, and a second angle of total reflection when the liquid content is against the circumferential interior surface. In an aspect, the filter trap apparatus can also include a light source that can be configured to emit a light beam incident on the face at an angle of incidence, and can include a light receiver. In an aspect, the index of optical refraction of the transparent circumferential prism can be selected such that the angle of incidence provides reflection of the light beam, so as to strike the light receiver, when the face has the first angle of total reflection, and can provide refraction of the light beam, so as to miss the light receiver, when the face has the second angle of total reflection.

In an aspect, a filter trap apparatus can further include the filter. According to additional aspects, the filter can include an ingress passage, an egress passage, and an intermediate passage. In one or more implementations, the filter can be configured to receive at the ingress passage samples of a therapeutic gas, remove the liquid droplets from the therapeutic gas to form a filtered therapeutic gas, and to deliver the liquid droplets through the intermediate passage, and output the filtered therapeutic gas from the gas egress passage.

In an aspect, the face can be an upper face, and the circumferential interior surface of the trap bowl can be, or can form, an upper circumferential interior surface. The transparent circumferential prism, according to one or more additional aspects, can also include a lower face, and the lower face can form a lower circumferential interior surface of the trap bowl. In or more implementations, the upper face and the lower face can form an included angle that, in an aspect, can open outwardly, circumferentially around the trap bowl. In an additional aspect, the upper face and the lower face can intersect at a vertex that can be circumferential around the trap bowl. In an exemplary aspect, the angle can be arranged symmetrically about a reference bisector line that, in turn, can extend outwardly from the vertex.

According to one or more implementations, the light source can be configured to emit the light beam as a collimated light beam, and to emit the collimated light beam in a direction approximately parallel to the reference bisector line. In an aspect, irrespective of rotational orientation of the trap bowl, the angle of incidence results in reflection of the light beam, striking the light receiver, when the face has the first angle of total reflection, and results in refraction of the light beam, missing the light receiver, when the face has the second angle of total reflection. In an aspect, the reference bisector line can extend in a reference cone that is circumferential about the trap bowl and contains the vertex. Further to one or more implementations, the included angle can be approximately 90 degrees. Also, in one or more implementations, the angle of incidence can be approximately 45 degrees.

In an aspect, the transparent circumferential prism can further include a light beam receiving face. In one related aspect, the collimated light beam can be incident to the light beam receiving face at a point of incidence, in an arrangement where a reference plane tangential to the light beam receiving face at the point of incidence normal to the collimated light beam. The light beam receiving face, in one or more implementations, can be a bevel that extends circumferentially around an outer surface of the trap bowl.

One or more disclosed additional embodiments also pertain to a filter trap apparatus that, in an aspect, can include a trap bowl configured to accumulate liquid droplets from a filter, as a liquid content. In an aspect, the trap bowl can include a section that extends in a vertical direction, and can include a transparent vertical prism. The transparent vertical prism can, according to an aspect, include a face that can form a vertical transparent surface facing against a content of the section. In an additional aspect, the face can be configured to provide a first angle of total reflection when content of the section is a gas, and a second angle of total reflection when the content of the section is the liquid content. An exemplary filter trap apparatus according to one or implementations can also include a light source, configured to emit a light beam incident on the face at an angle of incidence, and a light receiver. In an aspect, the angle of incidence, in combination with certain relations or ratios of indices of optical refraction, can provide reflection of the light beam, so as to strike the light receiver, when the face has the first angle of total reflection, and provide refraction of the light beam, so as to miss the light receiver, when the face has the second angle of total reflection.

In one or more implementations, the filter trap apparatus can also include an adjustable emitter/receiver support that can include a support element configured to attach to the optic emitter/receiver. In an aspect, the adjustable emitter/receiver support can also include a selectively actuated elevating support that supports the optic emitter/receiver at a selective elevation in the vertical direction.

In an aspect, the face can be a first face, and the vertical transparent surface can be a first vertical transparent surface. According to an additional aspect, the transparent vertical prism can further include a second face, and the second face can faun a second vertical transparent surface facing against the content of the section. In an aspect, the second face can also provide the first angle of total reflection when the content of the section is the gas, and the second angle of total reflection when the content of the section is the liquid content.

One or more disclosed embodiments pertain to a filter trap apparatus that, in aspect, can include trap bowl configured to accumulate liquid droplets from a filter, as a liquid content. In an aspect, the trap bowl can include a transparent circular section that can extend in a vertical direction. The transparent circular section, according to one or more aspects, can be formed of a material having an optical index of refraction. In one implementation, the filter trap apparatus can include an offset light source, configured to emit a light beam that is incident on an outer surface of the transparent circular section. In an aspect, at a point of incidence, the light beam can include a vector component parallel to a reference line that is tangential to the point of incidence, in combination with a vector component that is normal to the reference line at the point of incidence. According to one or more implementations, the filter trap apparatus can include an offset light receiver. As described above, in one or more aspects, the material for the transparent circular section can be formed of a material having a particularly selected optical index of refraction. Such aspects can include selecting the optical index of refraction such that, when a gas content is against the transparent section, the light beam is refracted along a first path, and when the liquid content is against the transparent section the light beam is refracted along a second path, wherein the first path is incident on the light receiver, and the second path misses the light receiver.

Other features and aspects of the disclosure will be apparent from the following detailed description, the drawings, and the claims.

BRIEF DESCRIPTION OF THE DRAWINGS

The features and advantages of the present disclosure will be more fully understood with reference to the following, detailed description when taken in conjunction with the accompanying figures, wherein.

DETAILED DESCRIPTION

The present disclosure generally relates to trapping specific materials suspended in or otherwise carried by a gas that, upon removal by specialized filtration and collection in a trap container, aggregate into a liquid state. The specific materials to be removed and collected in the trap container can include, for example, water vapor, other liquids in a vapor state, other nebulized liquids, nebulized medical solutions and suspensions, etc. In some implementations, the removal and trapping of the materials can be in the context of delivery of therapeutic gas to patients (e.g., patients receiving breathing gas, which can include nitric acid and other therapeutic gas, from a ventilator circuit). For example, implementations can include removal of such specific materials from a sample of a breathing gas passing through an inspiratory limb, prior to passing the sample through a sampling device. The sampling device can be configured to continuously confirm at least dosing (e.g., nitric oxide concentration, etc.) as well as other parameters (e.g., nitrogen dioxide concentration, oxygen concentration, etc.). can be installed in between the source of breathing gas and the sampling device, which may reduce contamination, for example, improving operation and/or longevity of the sampling device.

The concept of filtering suspended or entrained water vapor or other liquid components before a sample gas reaches a sampling device may be referred to at times as a "water trap," or "filter trap." However, the present disclosure relates to some implementations that can remove more than just water, such as, for example, various nebulized medications.

The terms liquid particles and/or particles are used herein in their broadest to encompass any and all of particles, liquid or solid, organic or inorganic, which could be in the gas flow such as, but not limited to, nebulized medical solutions and suspensions, aerosols, moisture from humidified air, or other contaminants present in patient breathing circuit resulting from treatments delivered via the breathing circuit. At times the term liquid particles, particles, matter, or the like are used individually or to refer to a common group of material to be removed.

The terms "filter" and "filtration" are used herein in their broadest sense to encompass any and all of various types and degrees of removal or separation of liquid from gas, and may also include removal of other non-liquid particulates if present in some cases.

Figure 1A:
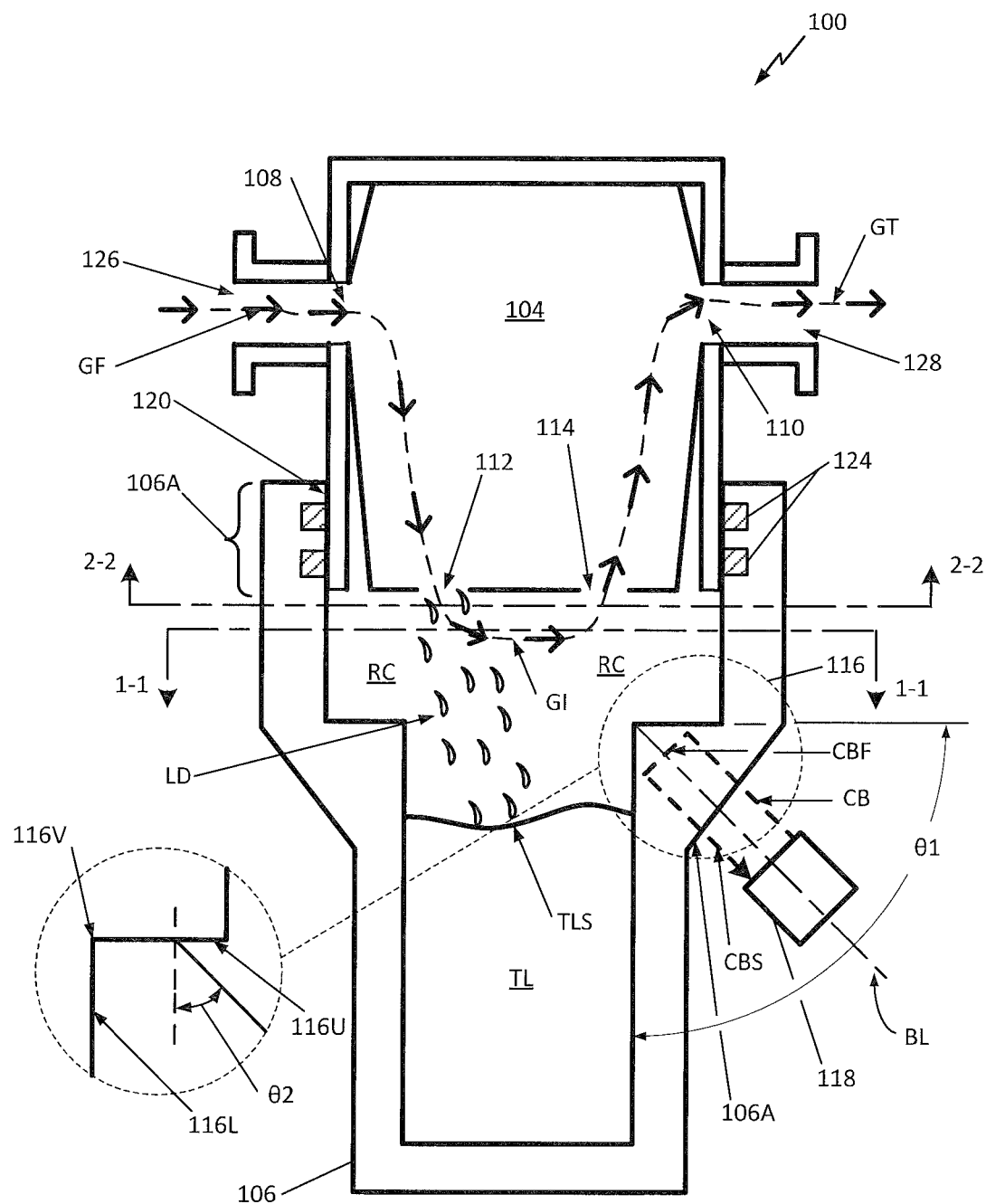
FIG. 1A illustrates a front cross sectional view of one implementation of a filter and fill level detecting trap assembly, including a circumferential prism and angled light beam emitter/detector, according to one or more embodiments, and an example aspect of return reflection by the circumferential prism in response to an operational fill level.

FIG. 1A illustrates a front cross sectional view of one implementation of a filter and fill level detecting trap assembly 100, including a circumferential prism and light beam emitter/detector, according to one or more embodiments. FIG. 1A additionally illustrates an example aspect of return reflection by the circumferential prism, according to one or more embodiments, in response to an operational fill level.

Referring to FIG. 1A, the filter and fill level detecting trap assembly 100 can include a filter housing 102, shaped and dimensioned to hold a filter, such as the example filter 104, arranged above a trap bowl 106. Operations of the filter 104 can include receiving, through a filter ingress passage 108, a sample of a therapeutic gas, then removing liquid from the sample as liquid droplets LD and depositing them in the trap bowl 106, then expelling the filtered sample gas out of a filter egress passage 110. The filter 104 can include a filter first intermediate passage 112 allowing the liquid the liquid droplets LD to call into the trap bowl, and a filter second intermediate passage 114 for passage of the sample gas from the trap bowl 108 and out through the filter egress passage 110. Example flow of sample gas through the filter 104, and associated filling of the trap bowl 106 with liquid droplets LD, is described in greater detail later. Further detailed description of internal structure of the filter 104, though, is not necessary for persons of skill to attain an understanding of concepts of the disclosure that is sufficient to make and use examples employing one or more one or more embodiments, and is therefore omitted.

It will be understood that the FIG. 1A illustrated shape and relative dimension of the filter housing 102 and filter 104 are only for purposes of example, and are not intended to the scope of this disclosure or the implementations for practicing according to its concepts.

Referring to FIG. 1A, in one or more implementations the trap bowl 106 can include a circumferential prism 116. In an associated aspect, at least such portions of the trap bowl 06 forming the circumferential prism 116 can be transparent.

It will be understood that "transparent," in the context of the trap bowl 106, is not limited to "see-through" visibility to the naked eye. For example, persons of ordinary skill will understand that transmittance that is within the meaning of "transparent can depend, at least in part, factors such as intensity of collimated light beam CB, length of the optical path (determined at least in part by the thickness and size of the trap bowl 106), cross-sectional dimensions of the circumferential prism 116, and sensitivity of the light detector portion of the optical transmitter/receiver 118.

In one implementation, the circumferential prism 116 can be integral to the trap bowl 106, for example, as a particular configuration of external surfaces of the trap bowl 106, as shown in FIG. 1A. In other implementations, of which examples are described in greater detail later in this disclosure, the circumferential prism 116 can be fainted separately and attached to the trap bowl 106.

In an aspect, the circumferential prism 116 can include an upper prism face 116U, and a lower prism face 116L that can form, viewed in cross section, a V-shaped arrangement of circumferential faces forming an included angle θ1 that opens in an outward direction, symmetrically about a bisector line BL, from a vertex 120V.

Figure 1B:
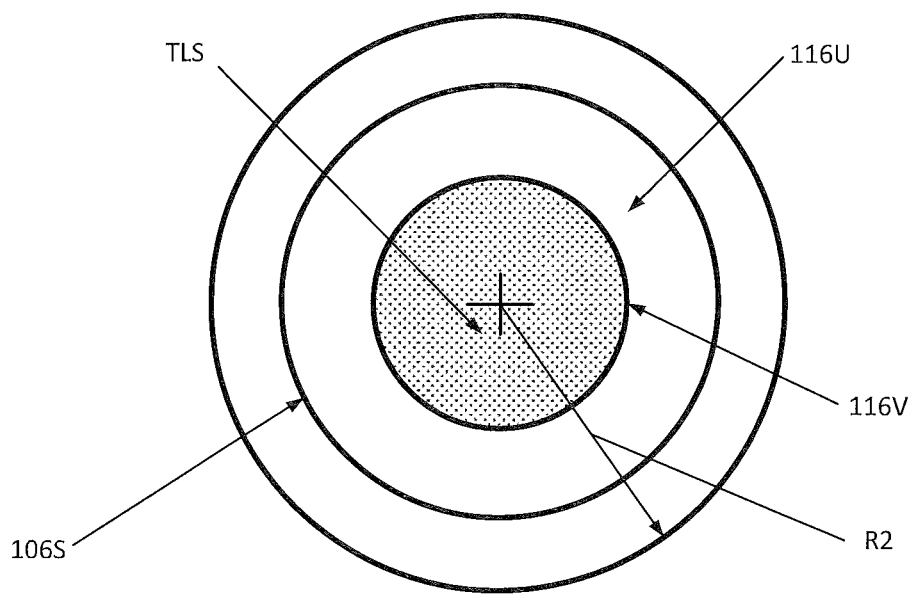
FIG. 1B illustrates an elevation view, from the FIG. 1A cut-plane projection 2-2, of a portion of the FIG. 1A trap bowl, showing an upper prism face of an exemplary circumferential prism according to or more embodiments.

FIG. 1B illustrates an elevation view, from the FIG. 1A cut-plane projection 2-2, of a portion of the FIG. 1A trap bowl 106, showing the circumferential configuration of the upper prism face 116U and the vertex 116V. Viewed from the FIG. 1A cut-plane projection 2-2 the lower prism face 116L, although not explicitly visible, is under and aligned with the upper prism face 116U.

Referring to FIG. 1A, the filter and fill level detecting trap assembly 100 can include an optical transmitter/receiver 118 that can be configured, for example, to both emit a collimated light beam (hereinafter "CB"), and detect receipt of such light. In an aspect, the optical transmitter/receiver 118 can be configured and arranged to emit CB in a direction parallel to, or approximately parallel to the bisector BL of the included angle θ1 between the upper prism face 116U and lower prism face 116L. In an aspect, the trap bowl 106 can have an exterior light beam receiving face 106A, for receiving CB from the emitter of the optical transmitted/receiver 118. The exterior light beam receiving face 106A, for example, can be a circumferential bevel. The circumferential bevel can be configured perpendicular to the bisector line BL. Since CB is parallel or approximately parallel to the bisector line BL, CB will strike the exterior light beam receiving face 106A (i.e., the circumferential bevel) at a normal incidence, which will avoid refraction of the CB. The collimated beam CB will therefore proceed to strike the upper prism face 116U at an angle of incidence θ2 that is approximately one-half of the included angle θ1.

An example selection of the optical refraction index, which will be referred to as "N1," for the material forming the transparent portion of the trap bowl 106 through which CB passes, to provide detection of the top surface TSL rising above the circumferential prism 116 will now be described.

Referring to FIG. 1A, until the top surface TSL of the trapped liquid TL reaches the upper prism face 116U, the substance within the trap bowl 106 against that upper prism face 116U will be air, or another gas, without substantial water content. The index of optical refraction of dry air or a dry gas will be referred to as "N2." For purposes of this description, N2 will be approximated as integer 1. When the surface TSL of the trapped liquid TL reaches the upper prism face 116U, water or another liquid having an index of optical refraction similar to water—which will be referred to as "N3," will be against the upper prism face. For purposes of this description, assuming the trapped liquid TL is water, N3 can be approximated as 1.5.

According to Snell's Law, if the angle of incidence θ2 of CB to the upper prism face 116U meets or exceeds the total reflection angle, "TFA," as defined in Equation (1) below, CB will be totally reflected from the upper prism face 116U, and will depart as a first totally reflected light beam (hereinafter "CBF"):

$$\text{TFA} = \sin^{-1}(N3/N1) \qquad \text{Equation (1)}$$

For purposes of illustration, an example θ1 value of approximately 90 degrees will be assumed, e.g., the upper prism face 116U being approximately perpendicular to the lower prism face 116L. Therefore, assuming CB is aligned with the bisecting line BL, the angle of incidence θ2 will be one-half of θ1, i.e., approximately 45 degrees.

The necessary value of N3 that will result in total internal reflection of CB (on the assumption that θ2 is approximately 45 degrees) can be solved by plugging 45 degrees and N1=1 into Equation (1), as follows $$45 = \sin^{-1}(1/N3) \rightarrow \sin(45) = 1/N3 \rightarrow N3 = 1/\sin(45) \approx 1/0.707, \text{ or } 1.41$$

Accordingly, if the index of refraction of the transparent material of the trap bowl 108 through which CB passes to hit the upper prism face 116U is greater than 1.41, CB will be totally reflected from the upper prism face 116U.

For purposes of illustration, transparent polycarbonate, having an optical index of refraction of approximately 1.6, will be used as an example transparent material of the trap bowl 106 through which CB passes to hit the upper prism face 116U. Since 1.6 is greater than 1.41, CB will be totally reflected by the upper prism face 116U. In fact, plugging N3=1.6 and N1=1 into Equation (1) yields the following value for the total reflection angle TFA:

$$\sin^{-1}(1/1.6) \approx 38.5 \text{ degrees.}$$

As described above, the angle of departure of CBF from the upper prism face 116U is the same as θ2, approximately 45 degrees. Since, in the FIG. 1A example, the upper prism face 116L and lower prism face 116U are perpendicular, CBF strikes the lower prism face 116L with an angle of incidence the same as θ2, i.e., approximately 45 degrees. Assuming the upper surface TSL of the trapped liquid TL has not reached the lower prism face 116L, CBF will therefore be totally reflected by the lower prism face 116L, departing as the second totally reflected light beam (hereinafter "CBS"). The angle of departure (visible, but not separately labeled) for CBS is the same as θ2, i.e., approximately 45 degrees. Accordingly, CBS will return and strike the optical receiver (not separately visible in FIG. 1A) of the optical transmitter/receiver 118.

Figure 1C:
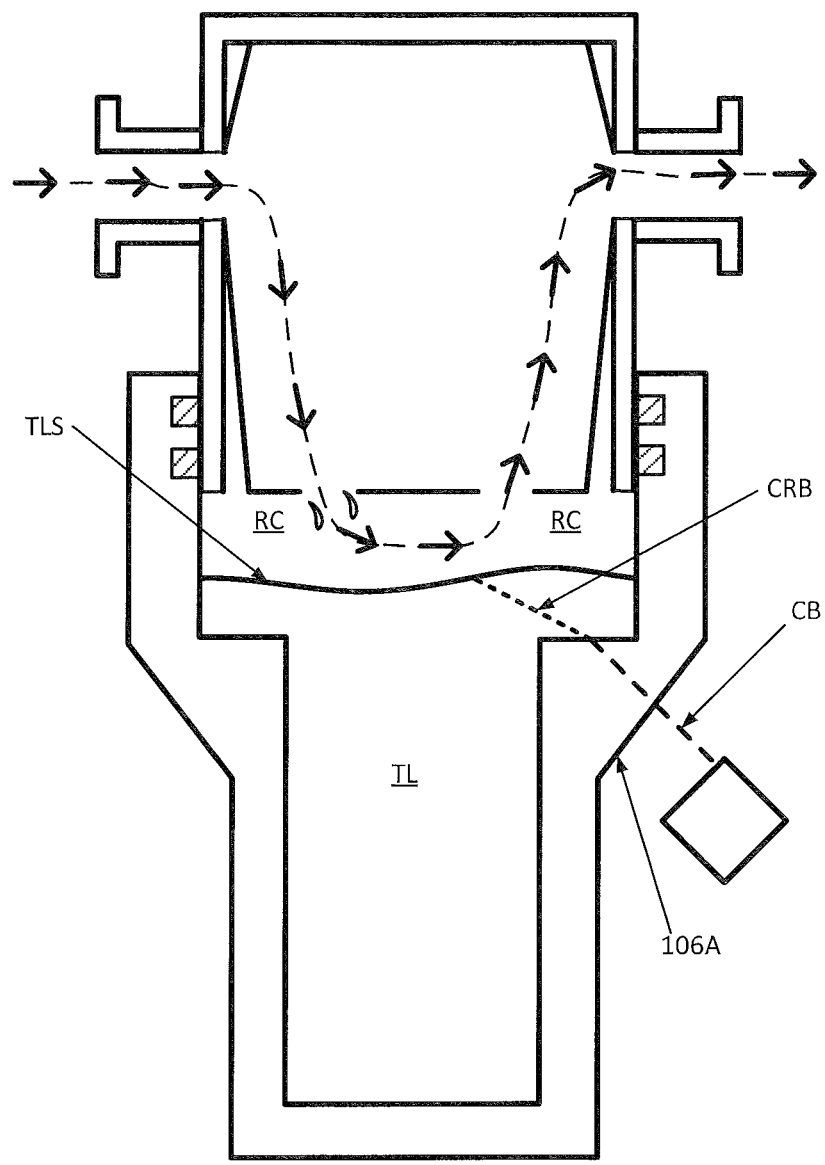
FIG. 1C illustrates the filter and fill level detecting trap assembly of FIG. 1A, with an example over-maximum fill level of fluid in the trap bowl, and a resulting detection by refracted non-return of the angled light beam, according to or more embodiments.

FIG. 1C illustrates the filter and fill level detecting trap assembly of FIG. 1A, with an example over-maximum fill level the fluid TL in the trap bowl 106, and a resulting refracted path of CB. Referring to FIG. 1C, in the depicted over-maximum fill state the substance of TL against the upper prism face 116U will be water or a similar characteristic fluid, having an index of refraction N2 of approximately 1.5. Continuing with polycarbonate (with an N3 of approximately 1.6) being the material forming the transparent region of the trap bowl 110 and substituting N2 for N1, Equation (1) yields the following value for the total reflection angle of CB in the FIG. 1C over-maximum state:

Total Reflection (over-fill state)=
$Sin^{-1}(1.5/1.6) \approx 70$ degrees.

Since 45 degrees is less than 70 degrees, CB will not be totally reflected from the upper prism face 116U and, instead, will continue into the fluid TL as a refracted beam (hereinafter "CRB, as labeled in the figures). Accordingly, no light beam will return to the optical receiver of the optical transmitter/receiver 118.

Figure 2:
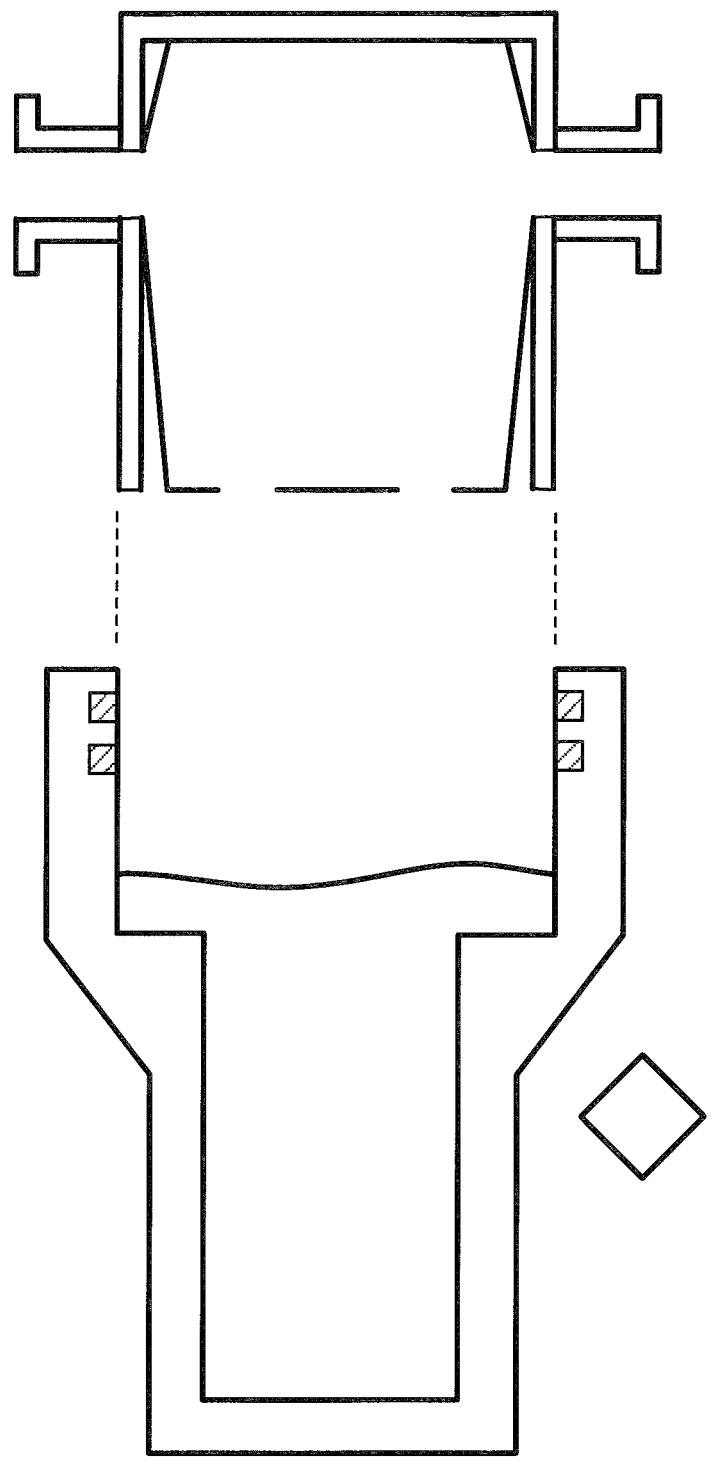
FIG. 2 illustrates, by partially exploded view, from the same projection as FIG. 1A, an example separation of the trap bowl including circumferential prism according to one or more embodiments, separated from the filter housing of the FIG. 1A.

In an aspect, the trap bowl 106 having the circumferential prism 116 can be selectively removed from the filter housing 102 for servicing or replacement. FIG. 2 illustrates, by partially exploded view of the filter and fill level detecting trap assembly 100, a removing of the trap bowl 106 from the filter housing 102. In an aspect, selective attachment and removal of the trap bowl 106 from the filter housing 102 can be provided, for example, by mechanical cooperation of a trap bowl attachment feature of the trap housing 102 and an upper attachment portion of the trap bowl 106.

Figure 3:
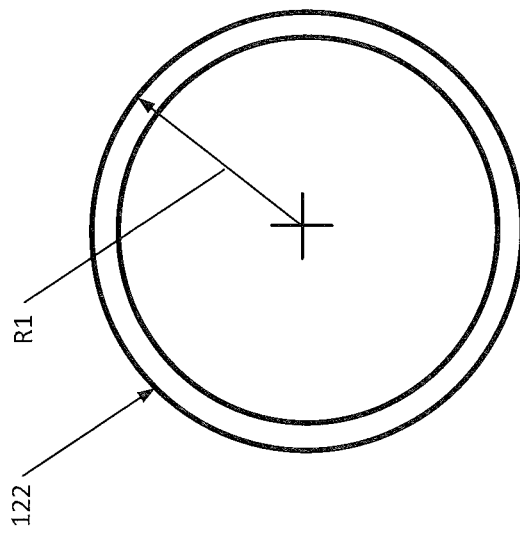
FIG. 3 illustrates an elevation view, from the FIG. 1A cut-plane projection 1-1, of one exemplary trap bowl attachment structure according to one or more embodiments.

One example structure for a trap bowl attachment feature of the filter housing 102 will be described in reference to FIGS. 1A, 1B, and 3, where FIG. 1C illustrates an elevation view, from the FIG. 1A cut-plane projection 2-2. Referring to FIGS. 1A and 3, in an aspect, a trap bowl attachment member 120 can be provided on a lower portion of the filter housing 102. One implementation of the trap bowl attachment member 120 can include a circular outer wall 122 (centered at CR) that, as seen in FIG. 1A, can project a distance D1 in a direction DR, and can have a radius R1, extending radially from the center CR. The direction DR can be, for example, "downward," i.e., toward earth.

Referring to FIGS. 1A and 1B, in an aspect, the trap bowl 106 can include an upper attachment portion 106A that can form a circular receptacle 106S having a radius R2, and depth D2. In an aspect, mechanical cooperation of the circular receptacle 106S and the circular outer wall 122 can be provided by setting the radius R2 slightly larger than R1, configuring outer threads (not explicitly visible in the figures) on the circular outer wall 122, and configuring corresponding inner threads on the circular receptacle 106S. For convenience, the outer threads on the circular outer wall 122, and corresponding inner threads on the circular receptacle surface 106S can be referenced collectively as "trap bowl attachment threads" (not explicitly visible in the figures). Whether the trap bowl attachment threads are "left hand" or "right hand" can be application-specific and, at least in part, may be a design choice.

In an aspect, the trap bowl 106 can be removed or separated as shown in FIG. 2 by rotating the trap bowl 106 in a first rotational direction (i.e. counter-clockwise or clockwise) until it separates from the filter housing 102. The trap bowl 106 can be replaced by aligning the circular outer wall 122 with the circular receptacle 106S, urging the trap bowl attachment threads into engagement, and rotating the trap bowl 106 in an opposite or second rotational direction (i.e., clockwise or counter-clockwise).

Referring to FIG. 1A, in one implementation at least one seal receiving groove (such as the representative example seal groove 124) can be formed in the circular outer wall 122, or the circular receptacle 106S, or both. The seal groove 124 or equivalent can be shaped and dimensioned to provide support for a corresponding liquid-tight seal member, such as the representative example liquid-tight seal member 126.

One example implementation of the liquid-tight seal member 126 can include a conventional "O ring."

As described above, the filter 104 can be configured with filter ingress passage 108, filter first intermediate passage 112, filter second intermediate passage 114, and filter egress passage 110. In one or more implementations, the filter housing 102 can include a filter housing ingress passage 128 and a filter housing egress passage 130. In an aspect, the filter housing 102 and filter 104 can be configured such that the filter housing ingress passage 128 substantially aligns with the filter ingress passage 108, and the filter housing egress passage 130 substantially aligns with the filter egress passage 110.

Referring to FIG. 1A, example operations of the filter 104, and resulting filling of the trap bowl 106 will be described. For convenience, FIG. 1A has a superposed diagram of a therapeutic gas flow, labeled in sections as "GF," "GI," and "GT." Also for convenience in description, the gas flow section GF, will be referred to as "unfiltered gas GF," the gas flow section GI will be referred to as "intermediate filtered gas GI," and the gas flow section GT will be referred to as "final filtered gas GT. Operations can include unfiltered gas GF entering the filter housing ingress passage 128, and passing into filter ingress passage 108, whereupon a first operation of the filter 104, which can be performed by structures and operations not explicitly visible in FIG. 1A, can remove some or all of the liquid particles from the therapeutic gas. The resulting intermediate filtered gas GI can then exit through filter first intermediate passage 112 and enter a remaining capacity space RC within the trap bowl 106. Falling downward through the filter first intermediate passage 112 and onto the top surface TSL can be liquid droplets LD that are removed from the unfiltered gas GF to obtain the intermediate filtered gas GI. Urged by pressure forcing the intermediate filtered gas GI into the remaining capacity space RC, the intermediate filtered gas GI can enter the filter second intermediate passage 114. In an aspect, the intermediate filtered gas GI can then pass through additional filtering structure (not visible in FIG. 1A) within the filter 104 to achieve the final filtered gas GT, which exits through the filter egress passage 110 and filter housing egress passage 130. In one alternative implementation, all or substantially all of the liquid removal function of the filter 104 can be performed prior to the intermediate filtered gas GI exiting the filter first intermediate passage 112.

Figure 4:
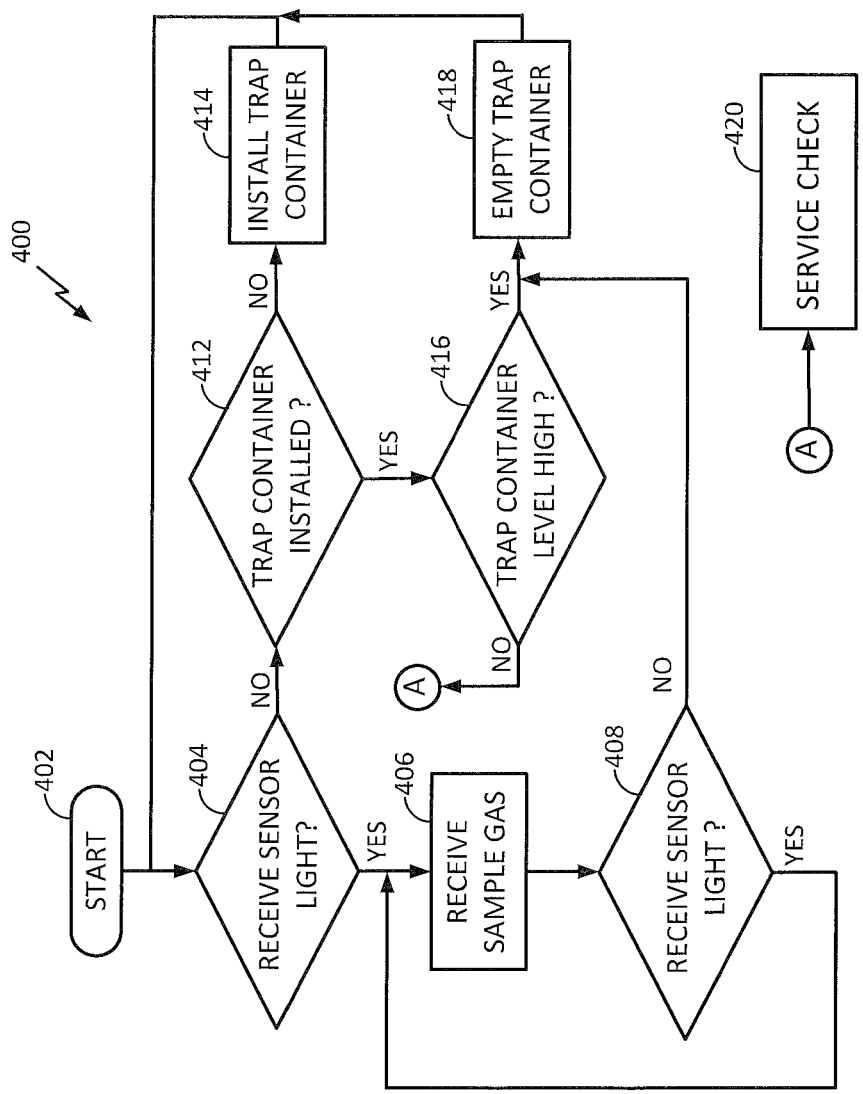
FIG. 4 shows a block representation of exemplary operations in a process of administering a gas therapy to a patient, including verifying trap bowl installation and fill level, in a method for delivery of therapy gas to a patient in accordance with one or more embodiments.

FIG. 4 shows a block flow 400 that represents exemplary operations in a process of verifying trap bowl installation and liquid level, in a method for delivery of therapy gas to a patient in accordance with one or more embodiments. For convenience, example performances of certain operations in the flow 400 will be described in reference to FIGS. 1A-1D. Referring to FIG. 4, operations in the flow 400 can start at a start event 402 and then proceed to decision block 404. Examples of a start event can include powering on a therapeutic gas delivery system, such as the example system 1400 described in reference to FIG. 14 later in this disclosure. In an aspect, operations in the start event 402 can include, for example, applying power to the transmitted/receiver 118, to emit the collimated beam CB.

Flow 400 can proceed from decision block 404 according to whether a reflected light beam is received. All illustration, operations at 404 can include determining whether FIG. 1A optical transmitted/receiver 118 received the reflected CBS beam. A "YES" indicates a trap bowl such as the trap bowl 106 is installed and has an operational level (e.g., anywhere from empty to just below maximum fill) of fluid, such as the fluid TL. The flow 400 can then proceed to 406 and perform operations of receiving a sample gas, e.g., from the therapeutic gas being delivered to the patient, then proceeding to 408 to determine whether the reflected light beam is still being received. If the answer at 408 is "YES," the flow can loop back to 406. It will be understood that the loop arrangement of blocks 406 and 408 does not necessarily mean a sequential loop. For example blocks 406 and 408 can represent a "continue until" process, e.g., continue receiving a sample gas until an interruption by, for example a cessation of receipt of the reflected light beam. Upon receiving, or affirmatively detecting a "NO" at 408, the flow 400 can proceed to 410 notify a user or attendant to empty the trap container, e.g., remove the trap bowl 106, empty it, and re-install it. The flow 400 can then return to 404 and, assuming the repeat the operations described above.

Example operations described above assume a "YES" at decision block 404. A "NO" at 404 indicates no receipt of the reflected light beam, e.g., optical transmitted/receiver 118 not received CBS beam. In one example resolution process, the flow can proceed to 412 and notify the user or attendant to each if the trap bowl is installed. If the user or attendant observes that the trap bowl is not installed, the flow 400 can proceed to 414 and await indication (e.g. pressing a user interface button) that the trap bowl has been installed, whereupon the flow 400 can return to 404. If the user or attendant observes, at 412, that the trap bowl is (or at least appears) installed, the flow 400 can proceed to 416 and notify the user or attendant to check if the trap bowl level is too high. For example, the user or attendant may check visually, if the trap bowl transparent portion described above is visibly transparent. If the user or attendant observes that the trap bowl is at an over-fill state, the flow 400 can proceed to 418 and await indication (e.g. pressing another user interface button) that the trap bowl has been emptied and re-installed, whereupon the flow 400 can return to 404. If at 416 the user or attendant observes, or otherwise determines that the trap bowl is not in an over-fill state, upon receipt from the user or attendant of such observation (e.g. pressing another user interface button), the flo4 400 may proceed to 418 and generate a notice for a service check.

Figure 5:
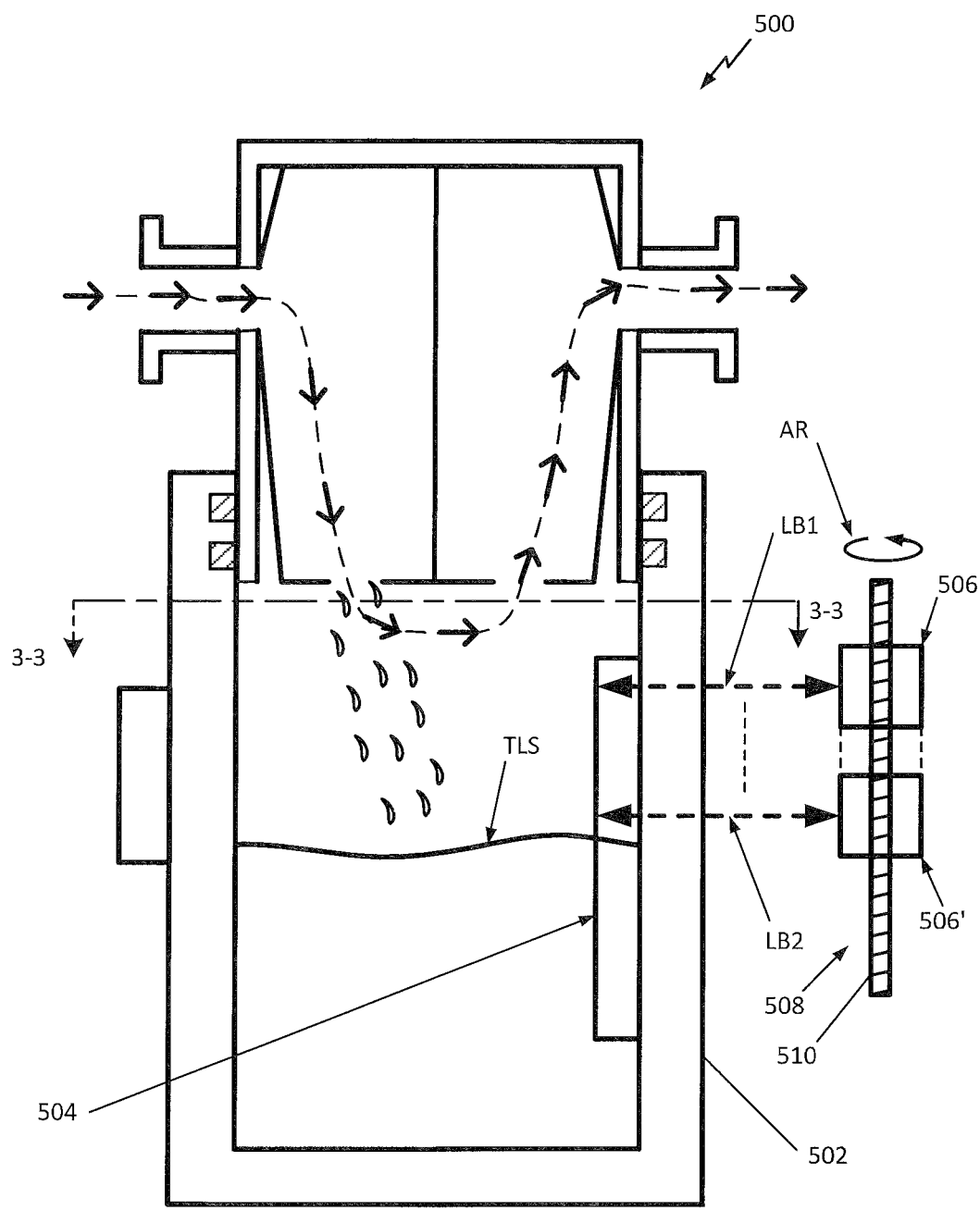
FIG. 5 illustrates a front cross sectional view of one implementation of a filter and trap assembly, including a fill level and trap bowl alignment detection by vertical prism and light beam, according to one or more embodiments, and certain features of example return reflection of the light beam in response to an operational fill level and properly installed trap bowl.
Figure 6:
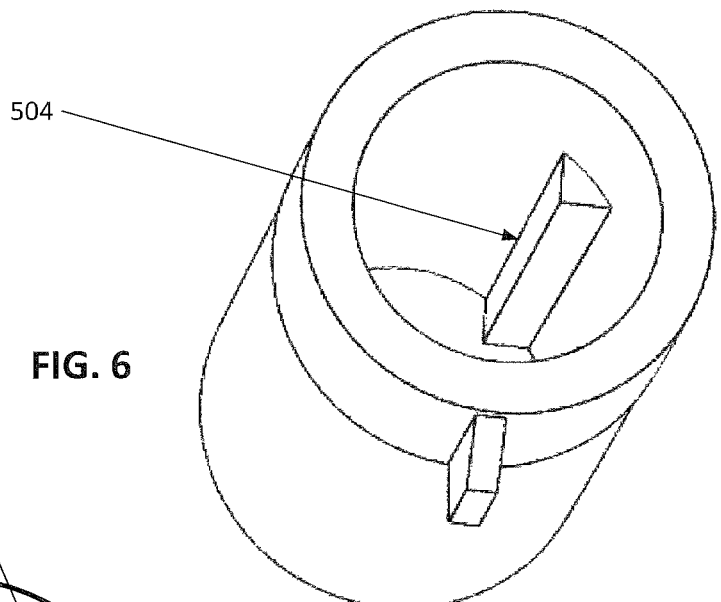
FIG. 6 shows one perspective view of an exemplary trap bowl with vertical prism, of the filter and an trap bowl assembly shown in FIG. 5, according to one or more embodiments.
Figure 7:
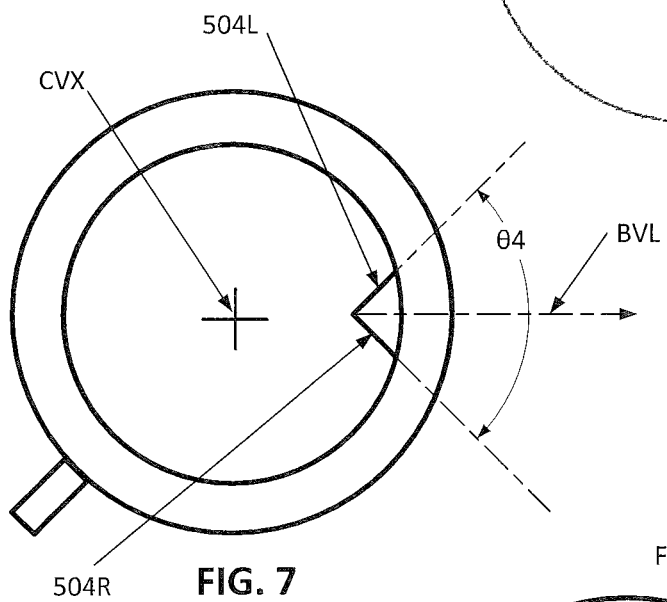
FIG. 7 illustrates a cross-sectional view from the FIG. 5 projection 3-3, without depiction of the light beam.
Figure 8:
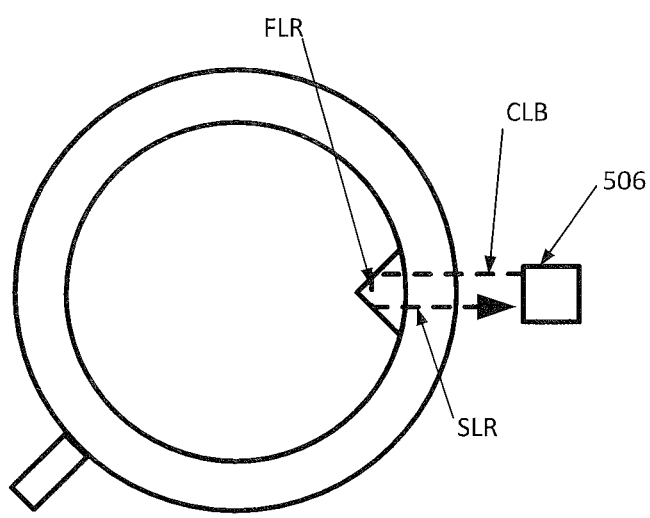
FIG. 8 illustrates a cross-sectional view from the FIG. 5 projection 3-3, without depiction of the light beam the example aspect shown in FIG. 5 of return reflection of the light beam in response to an operational fill level and properly installed trap bowl.

FIG. 5 illustrates a front cross sectional view of one implementation of a filter and trap assembly 500, including trap bowl 502 with vertical prism 504, and another optical emitter/receiver 506 according to one or more embodiments. FIG. 5 also illustrates in part, by superposed view (labeled "LB1") of incident and reflect light beam, an example aspect, according to one or more embodiments, of vertical prism detection of both operational fill level and properly installed trap bowl. FIG. 6 shows one perspective view of the exemplary trap bowl 502 with vertical prism 504, of the filter and a trap bowl assembly shown in FIG. 5 according to one or more embodiments. FIG. 7 illustrates, from the FIG. 5 projection 4-4, a cross-sectional view of the exemplary trap bowl 502 with vertical prism 504, omitting visible representation of a light beam from the optical emitter/receiver 506. FIG. 8 illustrates the FIG. 7 view, overlaid with graphical depiction of an example collimated light beam CLB generated by the optical emitter/receiver 506, as well as subsequent reflections back to the optical emitter/receiver 506, as will be described in greater detail later.

To focus on aspects and features shown departing from the filter and fill level detecting trap assembly 100, the filter and trap assembly 500 will be described assuming the same filter housing 102 and filter 104 as described in reference to FIGS. 1A-3. Similarly, it can be assumed that the trap bowl 502 with vertical prism 504 can have or can provide structure comparable to the circular receptacle 106S, for example, with inner threads (not explicitly visible in FIG. 5) configured to cooperate with threads, as described above, on the circular outer wall (visible in part in FIG. 5, but not separately labeled).

In an aspect, the filter and trap assembly 500 can include an adjustable emitter/receiver support 508 that can include a support element 510 configured to attach to the optic emitter/receiver 506. In one implementation, the adjustable emitter/receiver support 508 can include a lead screw 510, and the support element 510 can be a threaded sleeve (not explicitly visible in FIG. 5 secured to optic emitter/receiver 506 and through which the lead screw 510 can pass in a threaded engagement. In an aspect, the adjustable emitter/receiver support 508 can include a selectively actuated elevating support (not explicitly visible in FIG. 5). The selectively actuated elevating support, for example, can be servo motor (not explicitly visible in FIG. 5A), or manual actuation mechanism (not explicitly visible in FIG. 5A), or both, configured to selectively rotate the lead screw 510, as indicated by the directed arrow AR. Exemplary operation of the adjustable emitter/receiver support 508 is shown by a lower positioned phantom image, labeled 506', of the optic emitter/receiver 506.

Referring to FIG. 6, in an aspect the vertical prism 504 can be integral to the trap bowl 502, e.g., cast together in an injection mold. In another aspect, the trap bowl 502 can be formed sequentially as an interim trap bowl without the vertical prism 504, followed by attaching, e.g., by a transparent adhesive (not explicitly visible in FIG. 5) to an inner surface (visible in part in FIG. 6 but not separately numbered) of the interim trap bowl.

Referring to FIG. 7 the vertical prism 504 can be configured with a first vertical prism face 504L, and a second vertical prism face 504R, that can extend vertically, in parallel to one another, and in parallel to a vertically extending center axis CVX of the trap bowl 502. In an aspect, the first vertical prism face 504L and the second vertical prism face 504R can be arranged to form an included angle θ5, opening outward from a vertically extending vertex 504V. For purposes of illustration, an example value of the included angle θ5 will be picked approximately 90 degrees. In an aspect, the first vertical prism face 504L and second vertical prism face 504R can be configured such that the included angle θ5 is symmetrical about a vertical prism bisector line BVL. In addition, the first vertical prism face 504L and second vertical prism face 504R can be configured such that the vertical prism bisector line BVL extends radially from the vertically extending center axis CVX of the trap bowl 502.

Referring to FIG. 8, in an associated aspect, the optical emitter/receiver 506 can be configured and arranged to transmit a collimated light beam CLB that is aligned parallel to or approximately parallel to the vertical prism bisector line BVL. Further, referring to FIG. 5, the optical emitter/receiver 506 can be arranged to transmit the collimated light beam (hereinafter "CLB") in a plane (not explicitly visible in FIGS. 5-8) that is normal to the vertically extending center axis CVX.

Continuing to refer to FIG. 8, in an aspect, a transparent material forms at least the regions of the trap bowl 502 through which CLB travels to strike the first vertical prism face 504L, as well as the regions through which FLR and SLR travel, as will be further described in later paragraphs. Alternatively, the entire trap bowl 502 can be formed of transparent material.

According to an aspect, the optical emitter/receiver 506 can be arranged such that the collimated light beam CLB strikes an outer surface of the trap bowl 502 in a direction normal to a plane (not explicitly visible in the figures) tangential to the outer surface at that point. Therefore, assuming (for purposes of example) the included angle θ5 to be approximately 90 degrees, CLB will strike the first vertical prism face 504L with an angle of incidence (visible in FIG. 8 but not separately labeled) of 45 degrees. That is substantially the same as the incidence angle θ2, at which CB strikes the upper prism face 116U, i.e., angle θ2, which is 45 degrees.

FIG. 5 shows the upper surface TLS of the liquid fill TL to be below the height at which CLB strikes the first vertical prism face 504L. For purposes of description, it will be assumed that at least the transparent regions of the trap bowl 502 and its vertical prism 504 are formed of polycarbonate, as was assumed for examples described above. As also described above, the index of optical refraction of polycarbonate can be approximated as 1.6. Accordingly, plugging the value 1.6 into the Equation (1) example of Snell's Law of Total Reflection, and using the example angle of incidence of 45 degrees, CLB will be totally internally reflected by the first vertical prism face 504L. This will establish, as a result, the first laterally reflected beam FLR, followed by the second laterally reflected beam SLR, which will return and strike the optical emitter/receiver 506.

Figure 9:
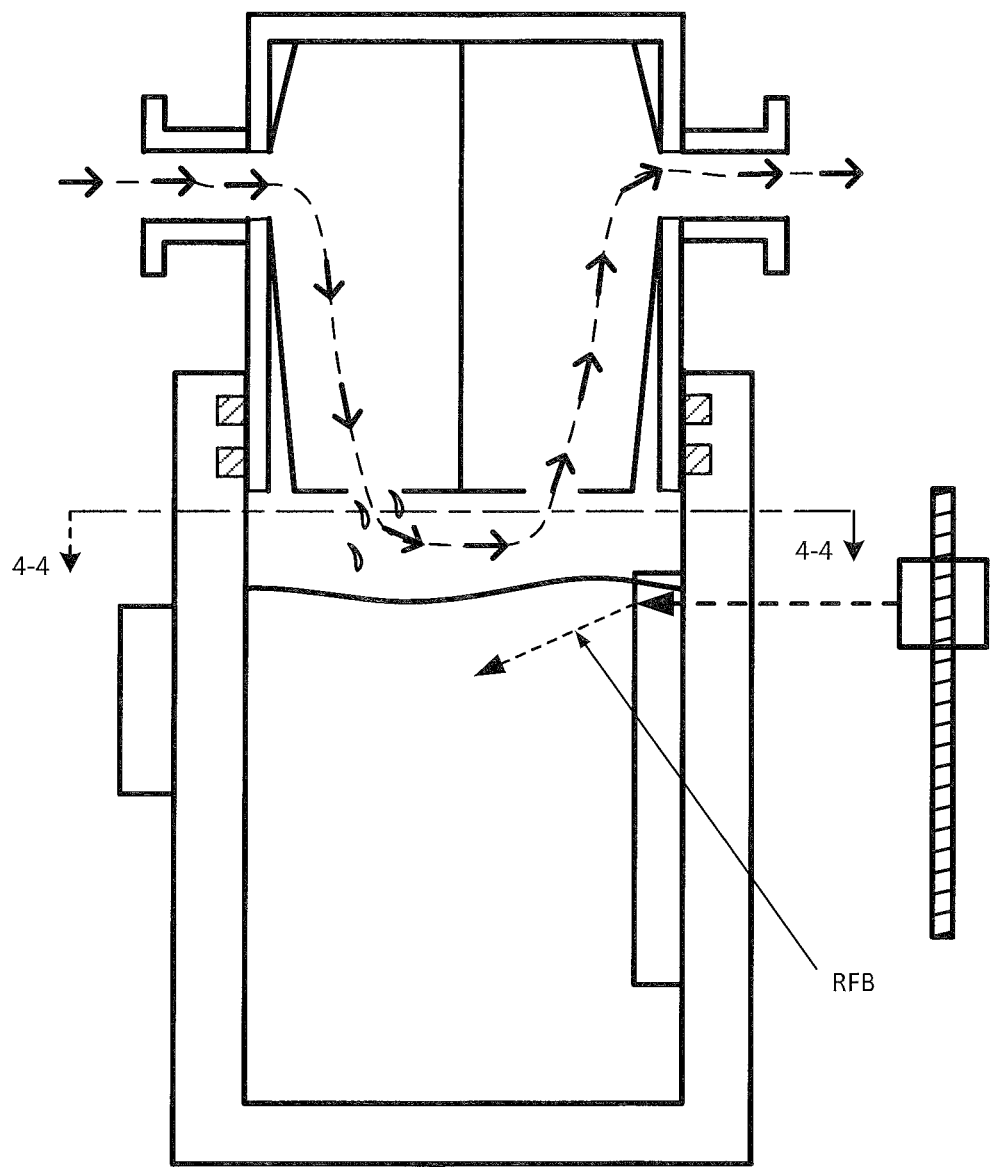
FIG. 9 illustrates, from the same front cross sectional view as FIG. 5, an example over fill state, and portions of a corresponding refracting non-return of the light beam, according to one or more exemplary embodiment.

FIG. 9 illustrates, from the same projection as FIG. 5, operation according to one or more exemplary embodiments, in response to the upper surface TLS of the liquid fill TL being at or above the point at which CLB strikes the first vertical prism face 504L. Assuming the polycarbonate material (N1 equal approximately 1.6) and referring to Equation (1), upon upper surface TLS of the liquid fill TL reaching the point where CLB strikes the first vertical prism face 504L, the Total Reflection Angle will be $\sin^{-1}$ (1.5/1.6), which is approximately 70 degrees. The angle incidence, namely 45 degrees, is less than 70 degrees. Accordingly, CLB will not be totally reflected from the first vertical prism face 504L. Instead, a substantial portion of CLB will continue into the fluid TL as a refracted beam (hereinafter "RFR," as labeled in the figures). Accordingly, whatever portion, if any, of the original CLB that returns to the optical receiver of the optical transmitter/receiver 506 will not be detected as a return.

Figure 10:
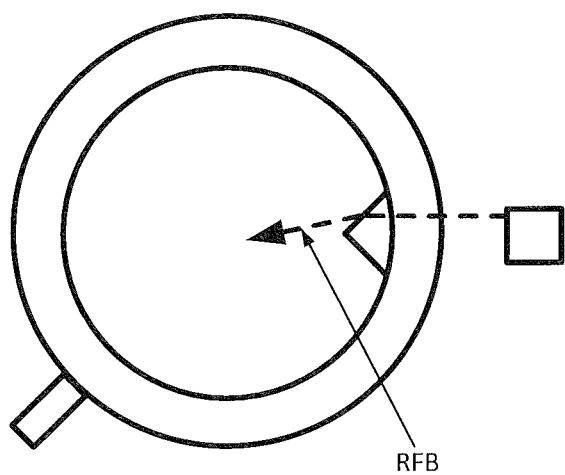
FIG. 10 illustrates a projection view, from the FIG. 9 projection 4-4, of the refracting non-return of the light beam, in response to the example over-filled state of a properly installed trap bowl according to one or more corresponding embodiments.

FIG. 10 illustrates, from the FIG. 9 projection 5-5, a cross-sectional view of the exemplary trap bowl 502 with vertical prism 504, another graphical depiction of the example collimated light beam CLB and refracted light beam RFR.

Figure 11A:
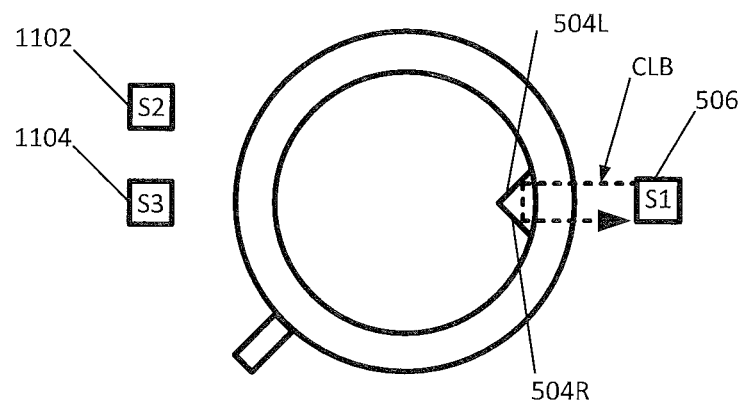
FIG. 11A illustrates a projection view, from the FIG. 5 projection 3-3, of one example implementation of a filter and vertical prism trap bowl assembly, including an offset optical detector, directed to detection of fill level and trap bowl installation, according to one or more embodiments.
Figure 11B:
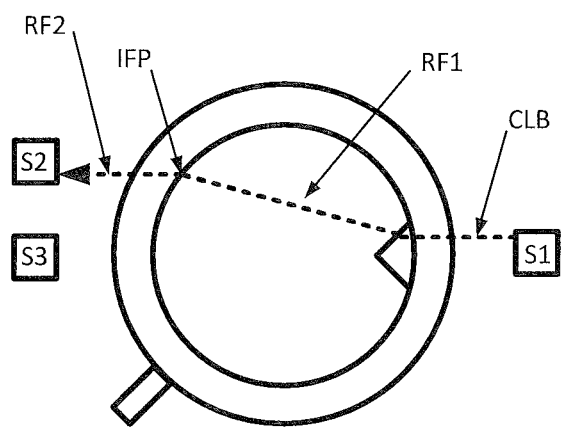
FIGS. 11B and 11C illustrate, from the same projection as FIG. 11A, additional capabilities that can be provided by the an offset optical detector.

FIG. 11A illustrates a projection view, from the FIG. 5 projection 3-3, of an example filter and vertical prism trap bowl assembly 1100. The filter and vertical prism trap bowl assembly 1100 can include the filter and vertical prism trap bowl assembly 500, configured in combination with an offset optical receiver 1102 (also labeled "S2"), and a diametrically opposed optical receiver 1104 (also labeled "S3"). For purposes of describing example operations, the receiver element of the optical transmitter/receiver 506 can be alternatively referred to as "first optical receiver 506," the offset optical receiver 1102 can be alternatively referred to "second optical receiver 1102," and diametrically opposed optical receiver 1104 can be alternatively referenced as "third optical receiver 1104." According to various aspects, the second optical receiver 1102 and third optical receiver 1104 can provide additional state detection capability. A first example capability is illustrated in FIG. 11A, and is similar to capability described above in reference to FIGS. 7 and 8, i.e., properly installed trap bowl 502 (namely, CLB aligned with the vertical prism bisector line BVL of the vertical prism 504), at an operational fill level (i.e., the top surface TLS of the liquid content TL being lower than CLB). A second example capability is illustrated in FIG. 11B, namely, a properly installed, but over filled trap bowl 502. A third example capability can detect and resolve down to two states, namely, an improperly installed (e.g., rotated) trap bowl 502 and a missing trap bowl 502.

Referring to FIG. 11A, assuming the example values as described above in reference to FIGS. 5 and 8 the emitted collimated beam CLB will strike the first vertical prism face 504L with an angle of incidence of 45 degrees. Assuming the example index of optical refraction for the vertical prism 504 (approximately 1.6), the angle of total reflectance is approximately 38 degrees. Accordingly, the reflections described in reference to FIGS. 5 and 8 will cause CLB to return, in substantial part, to the optical emitter/receiver 506.

Referring to FIG. 11B, and continuing with the assumption that the vertical prism 504 has an index of optical refraction (e.g., 1.6) close enough to the index of optical refraction of the water (e.g., 1.5), the 45 degree angle of incidence will be substantially less than the Angle of Total Reflectance. A significant portion of CLB will therefore continue into the content of the trap bowl 502, as a first refracted beam RF1, at an angle of refraction θ7. When the first refracted beam RF1 strikes, at point IFP, the interface of the content material of the trap bowl point and the material of the trap bowl 502, it will be refracted again, by an angle of refraction θ8 and continue as a second refracted beam RF2. Assuming a correctly set offset θ6, the second refracted beam RF2 will strike the offset (or second) optical sensor 1102.

Figure 11C:
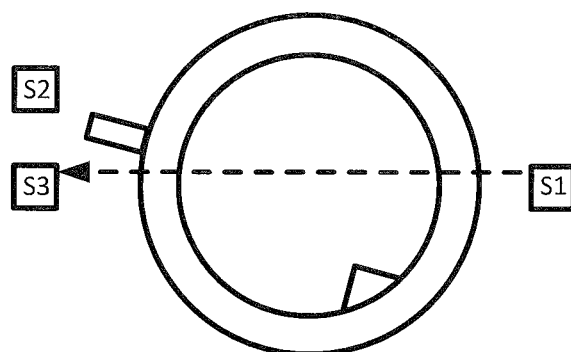

Referring to FIG. 11C, as described above, optical transmitter/receiver 506 aligns CLB with the vertical prism bisector line BVL when the trap bowl 502 is correctly installed. Therefore, when the trap bowl 502 is rotated as shown in FIG. 11C, CLB will strike the outer surface of the trap bowl 502 in a direction substantially normal to that outer surface. Accordingly, irrespective of interfaces of different indices of optical refraction, CLB will pass through the center axis CVX, and therefore hit the third optical sensor 1104. There may be ambiguity in state detection, though. For example, if the trap bowl 502 is missing (not explicitly shown in FIGS. 11A-11C), CLB will also continue in its original launch direction and hit the third optical sensor 1104.

Figure 12:
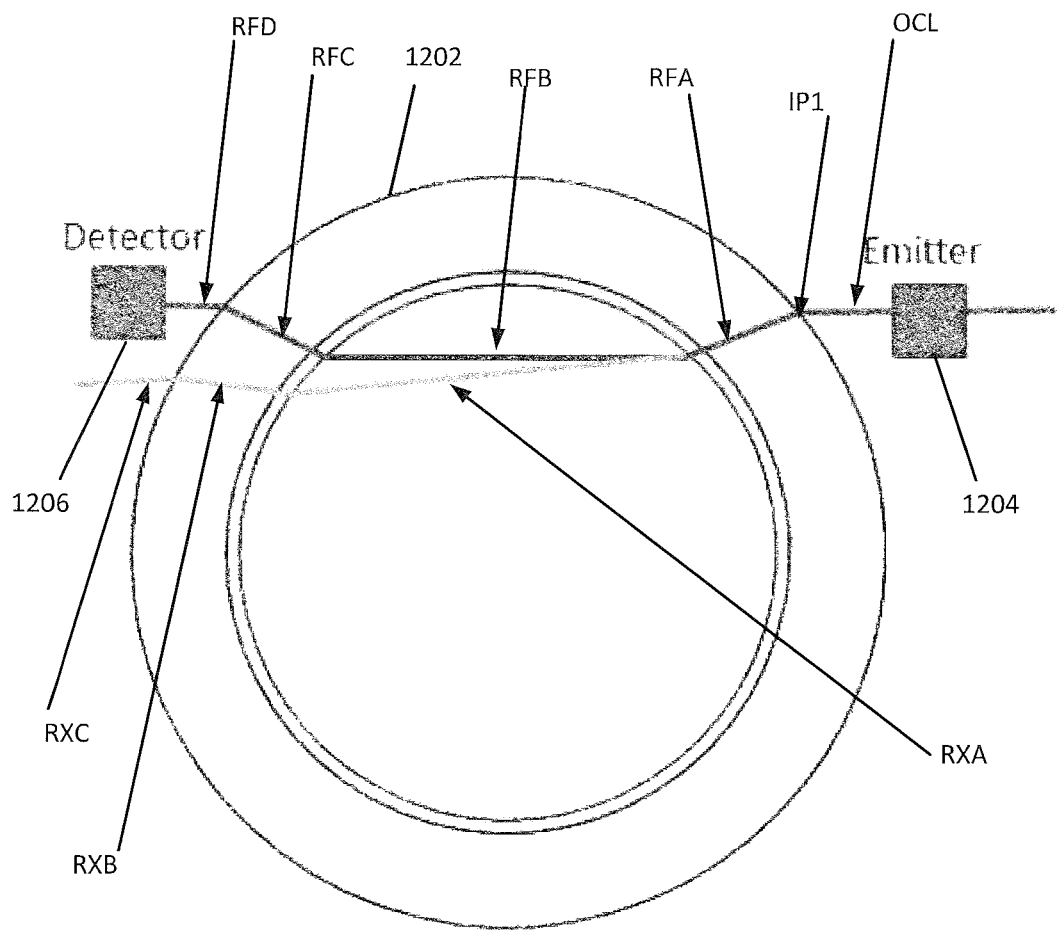
FIG. 12 illustrates a projection view, from the projection 3-3 of FIG. 5, of another implementation of a filter and trap assembly, including an offset emitter beam, and offset detector, providing a refraction based fill level detection according to one or more embodiments.

FIG. 12 illustrates a projection view, from the projection 3-3 of FIG. 5, of another implementation of a filter and trap assembly, which will be referred to as an "offset beam, refraction based filter and trap assembly 1200." An exemplary implementation of the offset beam, refraction based filter and trap assembly 1200 can include a transparent trap bowl 1202 (shown in part in FIG. 12), an offset optical emitter 1204 and offset optical detector 1206.

In an aspect, the offset optical emitter 1204 can be configured to emit an offset collimated light beam OCL, in a direction to be incident to an outer surface (visible in cross-section in FIG. 12) at an initial incidence point IP1. Assuming the index of optical refraction of the trap bowl to be, for example, approximately 1.6, the collimated light beam is refracted and continues as RFA until it hits the interface between the transparent trap bowl 1202 and its content. It will be assumed, for example, that the content of the trap bowl 1202, at the interface, is air or another gas with an index of optical refraction of approximately 1. Therefore, the refracted beam RFA will be refracted again as RFB, and continue until it hits, at IP2, the interface from the content of the trap bowl 1202 to the trap bowl 1202. The beam can then proceed through refractions as RFC and RFD, until it strikes the offset optical receiver 1206.

The above-described sequence of refraction segments, RFA, RFB, RFC, and RFD, can be referred to as the "non-filled optical path." If the content of the trap bowl 1202 through which the light beam traverses is water, each of the refraction will be less. The resulting segments, labeled RXA, RXB, and RXC, result in the beam missing the offset optical receiver 1206. The described segments RXA, RXB, and RXC can be referred to as the "over-maximum fill state optical path."

Referring to FIG. 12, it will be understood that an aspect of OCL is that, at its initial incidence point IP1, it is not normal to the outer surface of the trap bowl 1202. Stated differently, OCL can have a vector component (labeled "VX") parallel to the tangent at the initial incidence point IP1, and a vector component (labeled "VY") that is normal to the tangent.

Figure 13:
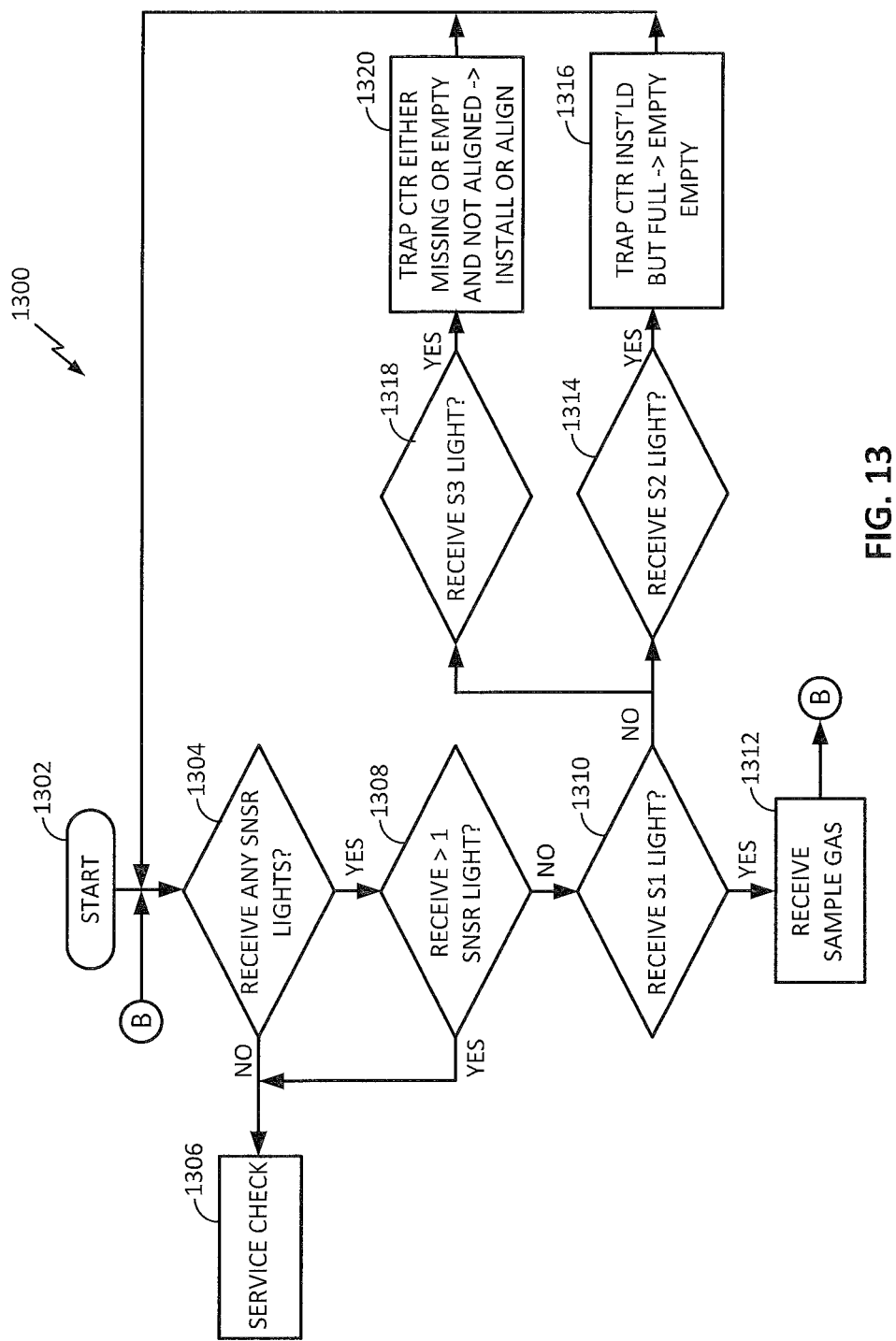
FIG. 13 shows a block flow representation of exemplary operations in a process, performed on or more of the FIG. 11A, 11B, 11C and FIG. 12 implementations, of detecting example trap bowl fill states, in a method for delivery of therapy gas to a patient in accordance with one or more embodiments.

FIG. 13 shows a block flow 1300, representing exemplary operations in a process, performed for example on the FIG. 11A-11C implementation (or with modification on the FIG. 12 implementation), of detecting example trap bowl fill states, in a method for delivery of therapy gas to a patient in accordance with one or more embodiments. Referring to FIG. 13, operations in the flow 1300 can start at a start event 1302 and then proceed to decision block 1304. Examples of a start event can include powering on a therapeutic gas delivery system, such as the example system 1400 that will be described in reference to FIG. 14. In an aspect, operations in the start event 1302 can include, for example, applying power to the optical transmitter/receiver 506 to emit the beam CLB. Flow 1300 can proceed from decision block 1304 according to whether any of the optical sensors received a signal. Referring to FIGS. 11A-11C, a failure to receive a signal at any of the first optical sensor 506, second optical sensor 1102 or third optical sensor 1304 can indicate a system failure. Accordingly, upon receiving a "NO" at decision block 1304, the flow 1300 can proceed to 1306 and notify a user or attendant of a need for servicing.

Referring to FIG. 13, assuming a "YES" at decision block 1304, the flow 1300 can proceed to decision block 1308. In an aspect, operations at decision block 1308 can include checking whether more than one of the optical sensors indicates receipt of a light beam. For example, assuming the set optical sensors to be the first optical sensor 506, second optical sensor 1102, and third optical sensor 1104, operations can include checking to determine if two or more of the set indicates receipt of a light beam. If the answer at 1308 is "YES" the flow 1300 can proceed to 1306 and, for example, notify the user or attendant of a need for servicing. If the answer at 1308 is "NO," the flow 1300 can proceed to 1310, where operations can determine whether the first optical sensor (e.g., the optical transmitter/receiver 506) has received a light beam. Referring to FIGS. 11A-11B, if the answer at 1301 is "YES," the flow 1300 has effectively determined that the trap bowl (e.g., trap bowl 502) is properly installed and at an operational fill level (i.e., has remaining capacity to receive liquid droplets LD). In response, the flow 1300 can proceed to 1312 and perform operations of receiving a sample gas, e.g., from the therapeutic gas being delivered to the patient, then return to 1310 to determine whether the reflected light beam is still being received (e.g., by the first optical sensor 506).

Continuing to refer to FIG. 13, if the initial answer at the answer at 1310 is "NO" or becomes "NO" during any iteration of the 1310-1312 loop, the flow 1300 proceed to decision block 1314. Operations at 1314 can include determining whether the second optical sensor (e.g., second optical sensor 1102) is receiving a light beam. Referring to FIG. 11B, if the answer at 1314 is "YES," the flow 1300 has determined that the trap bowl (e.g., trap bowl 502) is properly installed, but an over-maximum fill state. Accordingly, the flow 1300 can proceed to 1316 notify a user or attendant to empty the trap container, e.g., remove the trap bowl 502, empty it, and re-install it. The flow 1300 can then return to 1304 and repeat operations described above.

If, however, the answer at 1314 is "NO," the flow 1300 can proceed to 1318 and determine whether a light beam is being received at the third optical sensor (e.g., at the third optical sensor 1104). Referring to FIG. 11C, if the answer at 1318 is "YES," the flow 1300 has determined that the trap bowl (e.g., trap bowl 502) is either missing, or improperly installed (e.g., is rotated as shown in FIG. 11C). Accordingly, the flow 1300 can proceed to 1320 and notify a user or attendant that the trap=bowl (e.g., trap bowl 502) is either missing, or improperly installed. The flow 1300 can, for example, await indication at 1320 (e.g., detecting the user or attendant pressing an interface button) that the trap bowl has been properly installed, the flow 300 can return to 1304.

Figure 14:
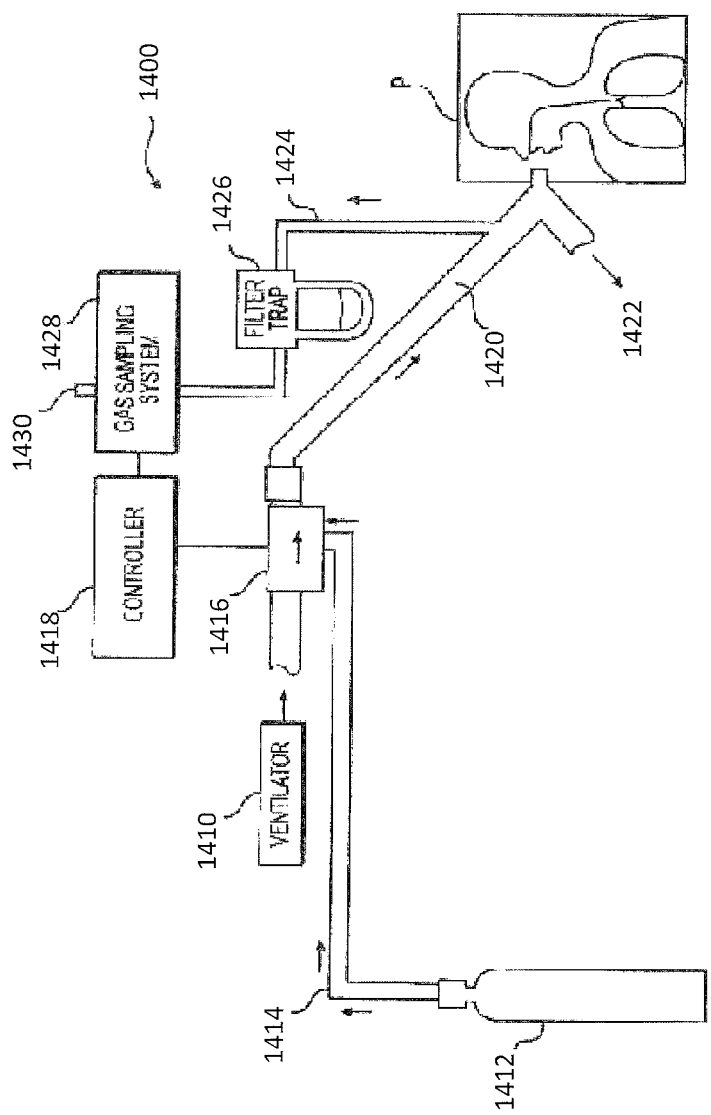
FIG. 14 illustratively depicts aspects of one exemplary implementation of a filter and level detecting trap assembly in a breathing gas supply apparatus, in accordance with one or more embodiments.

FIG. 14 illustratively depicts aspects of one exemplary implementation of a filter and level detecting trap assembly in a breathing gas supply apparatus, in accordance with one or more embodiments. This exemplary implementation relates to a breathing apparatus, and does not limit the other various implementations of filter assemblies according to this disclosure. Referring to FIG. 14, an apparatus 1400 is used with a ventilator 1410. A supply 1412 of supplemental or additive gas such as NO provides a supply to conduit 1414 and leads to a valve 1416 which may also be connected to the ventilator 1410. At any stage of breathing gas supply, other additional breathing materials such as nebulized drugs may be provided into a stream that travels via conduit 1420. A controller 1418 may actuate valves to control the ratio of NO and nebulized drugs to the mixture gas in conduit 1420. A patient inhales the content of conduit 1420 which may be considered as an inspiratory limb. The patients exhale or excess gas may be considered as an expiratory limb conduit 1422.

In this example, a conduit 1424 is in fluid communication with the inspiratory limb and may be referred to as a sample gas line. A filter and trap assembly 1426 receives some or all of the sample gas. In an aspect, filter trap assembly 1426 may correspond to a filter and trap assembly 1100 such as described above. After being filtered by the filter trap assembly 1326, the gas is passed to a gas sampling system 1428, and may exhaust via exhaust outlet 1430.

The foregoing detailed descriptions are presented to enable any person skilled in the art to make and use the disclosed subject matter. For purposes of explanation, specific nomenclature is set forth to provide a thorough understanding. However, it will be apparent to one skilled in the art that these specific details are not required to practice the disclosed subject matter. Descriptions of specific applications are provided only as representative examples. Various modifications to the disclosed implementations will be readily apparent to one skilled in the art, and the general principles defined herein may be applied to other implementations and applications without departing from the scope of this disclosure. The sequences of operations described herein are merely examples, and the sequences of operations are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness. This disclosure is not intended to be limited to the implementations shown, but is to be accorded the widest possible scope consistent with the principles and features disclosed herein.

It will be apparent to those skilled in the art that various modifications and variations can be made to the methods and systems of the present description without departing from the spirit and scope of the description. Thus, it is intended that the present description include modifications and variations that are within the scope of the appended claims and their equivalents.

It will be understood that any of the steps described can be rearranged, separated, and/or combined without deviated from the scope of the invention. For ease, steps are, at times, presented sequentially. This is merely for ease and is in no way meant to be a limitation. Further, it will be understood that any of the elements and/or embodiments of the invention described can be rearranged, separated, and/or combined without deviated from the scope of the invention. For ease, various elements are described, at times, separately. This is merely for ease and is in no way meant to be a limitation.

The separation of various system components in the examples described above should not be understood as requiring such separation in all examples, and it should be understood that the described components and systems can generally be integrated together in a single packaged into multiple systems and/or multiple components. It is understood that various modifications may be made therein and that the subject matter disclosed herein may be implemented in various forms and examples, and that the teachings may be applied in numerous applications, only some of which have been described herein. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A filter trap apparatus, comprising:
  a trap bowl configured to accumulate liquid droplets from a filter, as a liquid content, comprising a transparent circumferential prism, having a face that forms a circumferential interior surface of the trap bowl, the face having a first angle of total reflection when a gas is against the circumferential interior surface, and a second angle of total reflection when the liquid content is against the circumferential interior surface;
  a light source, configured to emit a light beam incident on the face at an angle of incidence; and
  a light receiver, wherein the angle of incidence results in reflection of the light beam, striking the light receiver, when the face has the first angle of total reflection, and results in refraction of the light beam, missing the light receiver, when the face has the second angle of total reflection,
  wherein the face is an upper face, wherein the circumferential interior surface of the trap bowl is an upper circumferential interior surface, wherein the transparent circumferential prism further comprises a lower face, wherein the lower face forms a lower circumferential interior surface of the trap bowl, and wherein the upper face and the lower face form an included angle that opens outwardly, circumferentially around the trap bowl,
  wherein the upper face and the lower face intersect at a vertex, the vertex being circumferential around the trap bowl, and wherein the included angle is arranged symmetrically about a reference bisector line the extends outward from the vertex,
  wherein the light source is configured to emit the light beam as a collimated light beam, and to emit the collimated light beam in a direction approximately parallel to the reference bisector line, and
  wherein, irrespective of rotational orientation of the trap bowl, the angle of incidence results in reflection of the light beam, striking the light receiver, when the face has the first angle of total reflection, and results in refraction of the light beam, missing the light receiver, when the face has the second angle of total reflection.

2. The filter trap apparatus of claim 1, further comprising the filter, wherein the filter includes an ingress passage, an egress passage, and an intermediate passage, wherein the filter is configured to receive at the ingress passage samples of a therapeutic gas, remove the liquid droplets from the therapeutic gas to form a filtered therapeutic gas, deliver the liquid droplets through the intermediate passage, and output the filtered therapeutic gas from the gas egress passage.

3. The filter trap apparatus of claim 1, wherein the reference bisector line extends in a reference cone that is circumferential about the trap bowl and contains the vertex.

4. The filter trap apparatus of claim 1, wherein the included angle is approximately 90 degrees.

5. The filter trap apparatus of claim 4, wherein the angle of incidence is approximately 45 degrees.

6. The reference trap apparatus of claim 1, wherein the transparent circumferential prism further includes a light beam receiving face, wherein the collimated light beam is incident to the light beam receiving face at a point of incidence.

7. The filter trap apparatus of claim 6, wherein the included angle is approximately 90 degrees, the angle of incidence is approximately 45 degrees, and wherein the light beam receiving face is a bevel that extends circumferentially around an outer surface of the trap bowl.

8. The filter trap apparatus of claim 1, further comprising the filter, wherein the filter included an ingress passage, an egress passage, and an intermediate passage, wherein the filter is configured to receive at the ingress passage samples of a therapeutic gas, remove the liquid droplets from the therapeutic gas to form a filtered therapeutic gas, deliver the liquid droplets through the intermediate passage, and output the filtered therapeutic gas from the gas egress passage.

* * * * *